United States Patent
Lee et al.

(10) Patent No.: US 9,360,443 B2
(45) Date of Patent: Jun. 7, 2016

(54) NANO SCALE RESONATOR, NANO SCALE SENSOR, AND FABRICATION METHOD THEREOF

(71) Applicant: SAMSUNG ELECTRONICS CO., LTD., Suwon-si (KR)

(72) Inventors: Moon Chul Lee, Seongnam-si (KR); Duck Hwan Kim, Goyang-si (KR); In Sang Song, Osan-si (KR); Jea Shik Shin, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 520 days.

(21) Appl. No.: 13/668,760

(22) Filed: Nov. 5, 2012

(65) Prior Publication Data

US 2013/0214876 A1    Aug. 22, 2013

(30) Foreign Application Priority Data

Feb. 17, 2012   (KR) .......................... 10-2012-0016181

(51) Int. Cl.
*G01N 27/04*   (2006.01)
*H03H 9/24*   (2006.01)
*H03H 3/007*   (2006.01)
*H03H 9/02*   (2006.01)

(52) U.S. Cl.
CPC ............. *G01N 27/04* (2013.01); *H03H 3/0072* (2013.01); *H03H 9/2463* (2013.01); *B81B 2201/02* (2013.01); *H03H 3/0077* (2013.01); *H03H 2009/0244* (2013.01); *H03H 2009/02346* (2013.01)

(58) Field of Classification Search
CPC .............. H03H 3/0072; H03H 9/2463; H03H 2009/02346; H03H 2009/0244; H03H 3/0077; B81B 2201/02; B81B 2201/0271; B81B 2201/0292; G01N 27/04
USPC .......................... 333/186, 187; 257/414, 415
See application file for complete search history.

(56) References Cited

U.S. PATENT DOCUMENTS

| | | | |
|---|---|---|---|
| 7,385,334 B1 * | 6/2008 | Olsson et al. ................. 310/322 |
| 7,932,792 B2 * | 4/2011 | Kaunisto ............... B82Y 10/00 257/25 |
| 2008/0297276 A1 | 12/2008 | Jun et al. | |
| 2009/0289747 A1 * | 11/2009 | Duraffourg .......... H03H 3/0073 333/219.2 |
| 2010/0007443 A1 * | 1/2010 | Mohanty et al. .............. 333/188 |
| 2011/0143448 A1 | 6/2011 | Serban et al. | |

FOREIGN PATENT DOCUMENTS

| | | |
|---|---|---|
| JP | 2009-44158 A | 2/2009 |
| JP | 2009-264904 A | 11/2009 |
| JP | 2009-268084 A | 11/2009 |
| KR | 10-2006-0018466 A | 3/2006 |
| KR | 10-2007-0076965 A | 7/2007 |
| KR | 10-2008-0105731 A | 12/2008 |

* cited by examiner

*Primary Examiner* — Benny Lee
*Assistant Examiner* — Jorge Salazar, Jr.
(74) *Attorney, Agent, or Firm* — NSIP Law

(57) ABSTRACT

A nano scale resonator, a nano scale sensor, and a fabrication method thereof are provided. The nano scale resonator includes a resonance unit of nano scale configured to resonate based on an applied signal, and an anchor on a substrate, the anchor being configured to support the resonance unit, the anchor having an air gap within boundaries of the anchor, the resonance unit, and the substrate, the air gap being configured to reflect a vertical wave occurring in the resonance unit.

7 Claims, 8 Drawing Sheets

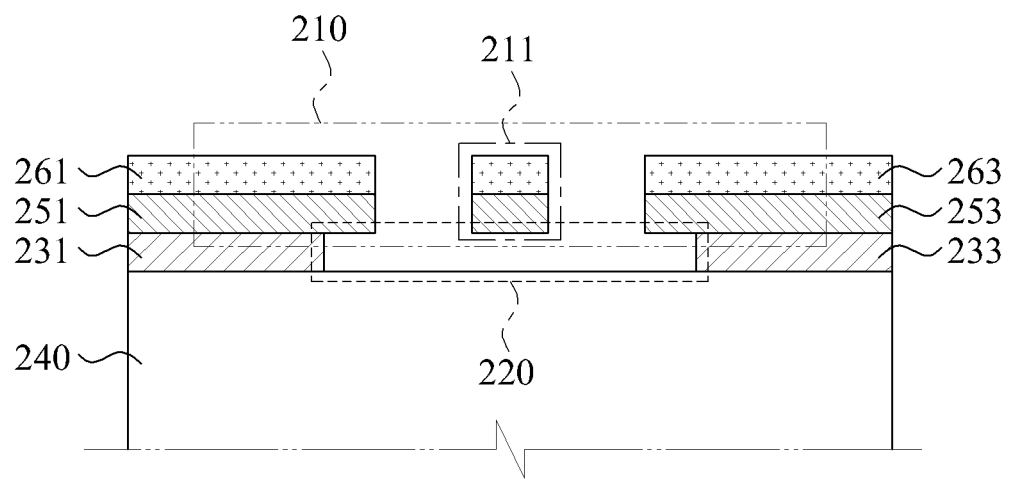
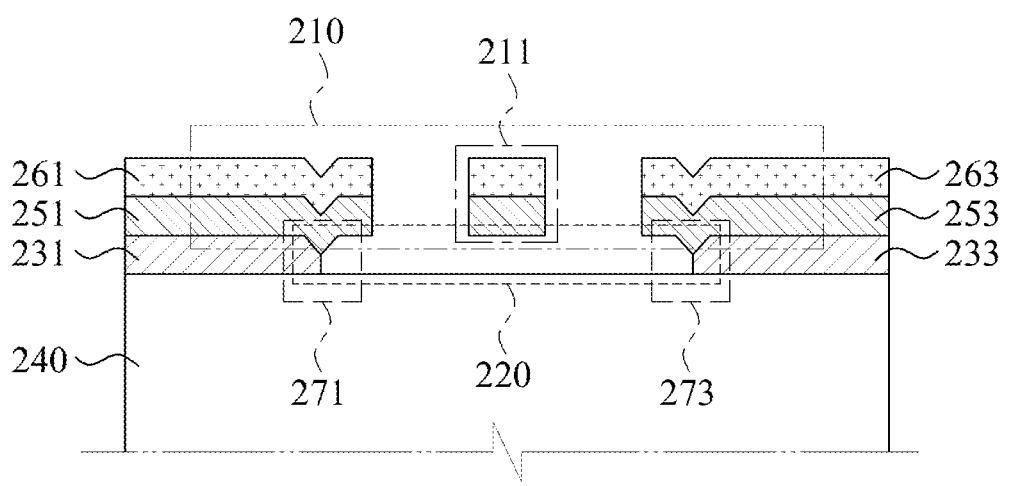

NANO SCALE RESONATOR, NANO SCALE SENSOR, AND FABRICATION METHOD THEREOF

CROSS-REFERENCE TO RELATED APPLICATION(S)

This application claims the benefit under 35 U.S.C. §119 (a) of Korean Patent Application No. 10-2012-0016181, filed on Feb. 17, 2012, in the Korean Intellectual Property Office, the entire disclosure of which is incorporated herein by reference for all purposes.

BACKGROUND

1. Field

The following description relates to a nano scale resonator, a nano scale sensor, and a fabrication method thereof.

2. Description of Related Art

With the rapid development in communication technology, high frequency technology corresponding to the communication technology is being developed. In an example of hardware communication technology, miniaturization of high frequency technology employed due to the corresponding miniaturization of wireless communication devices.

In an example, a resonator of a micro unit is fabricated using a micro electro mechanical systems (MEMS) process. However, constraints have been experience in the fabrication of resonators having superior quality factor (Q) values. In general, to increase a Q value of a resonator, either a resonator structure hardness has been increased or a planar type of resonator has been fabricated.

In an example, a planar type of MEMS resonator is fabricated to have a superior resonant frequency. However, a fabrication process of a planar type of MEMS resonator is difficult due to the membrane form of the fabricated planar type of MEMS resonator.

SUMMARY

In one general aspect, a nano scale resonator includes a resonance unit of nano scale configured to resonate based on an applied signal, and an anchor on a substrate, the anchor being configured to support the resonance unit, the anchor having an air gap within boundaries of the anchor, the resonance unit, and the substrate, the air gap being configured to reflect a vertical wave occurring in the resonance unit.

The nano scale resonator may further include that the resonance unit includes a first electrode, a resonance layer, and a second electrode, the first electrode being configured to receive the applied signal, the resonance layer being configured to resonate a signal based on the received signal, the second electrode being configured to output the resonated signal.

The nano scale resonator may further include that the resonance layer includes poly silicon, silicon nitride, or a metal based material.

The nano scale resonator may further include that the resonance unit includes one or more sub resonance units of nano scale.

The nano scale resonator may further include that the sub resonance units includes a linear shape, a circular shape, or a serpent shape.

The nano scale resonator may further include that the anchor includes a material having a resistivity that is of greater than or equal to 10 kΩcm.

In another general aspect, a nano scale sensor includes a sensing unit of nano scale configured to sense a bonding material to be combined with a surface processed material based on an electrical characteristic of the bonding material, and an anchor on a substrate, the anchor being configured to support the sensing unit, the anchor having an air gap within boundaries of the anchor, the sensing unit, and the substrate, the air gap being configured to reflect a vertical wave occurring in the sensing unit.

The nano scale sensor may further include that the sensing unit is further configured to sense the bonding material based on a change in resistance that varies based on the bonding material or a change amount of a resonant frequency that varies based on the bonding material.

The nano scale sensor may further include that the sensing unit includes one or more sub sensing units of nano scale.

In yet another general aspect, there is provided a fabrication method of a nano scale resonator, the method including sequentially depositing a sacrificial layer, a resonance layer, and a conductive layer on a substrate, patterning the deposited conductive layer to fit a shape of the nano scale resonator, depositing photoresist on the patterned conductive layer, opening a predetermined area of the deposited photoresist by emitting ultraviolet rays toward the predetermined area, depositing laser interference lithography dedicated resist on the opened area, performing a laser lithography process to fit a shape of one or more sub resonance units of nano scale, etching the conductive layer and the resonance layer to fit the shape of the sub resonance units, and forming an anchor on the substrate from the deposited sacrificial layer, the forming of the anchor including forming an air gap within boundaries of the formed anchor, a plane of the deposited resonance layer, and the substrate by removing a portion of the deposited sacrificial layer using etchant in a vapor state.

The method may further include that the sacrificial layer includes a silicon oxide based material or a silicon nitride based material.

The method may further include that the resonance layer includes nickel (Ni), nichrome (NiCr), chrome (Cr), or titanium (Ti).

The method may further include that the etching of the conductive layer and the resonance layer is performed by a reactive ion etching process using reactive gas with respect to ion acceleration.

The method may further include dicing the laser interference lithography dedicated resist deposited substrate to be in a chip shape.

The method may further include patterning the deposited sacrificial layer to fit a shape of a valley corresponding to a boundary between the formed air gap and the formed anchor, where the forming of the anchor includes removing the portion of the deposited sacrificial layer based on the valley in the sacrificial layer.

The method may further include that the portion of the deposited sacrificial layer is removed by injecting etchant through a via-hole that is connected to the deposited sacrificial layer.

Other features and aspects will be apparent from the following detailed description, the drawings, and the claims.

BRIEF DESCRIPTION OF THE DRAWINGS

FIG. 2A is a cross-sectional view illustrating an example of a nano scale resonator.

FIG. 2B is a cross-sectional view illustrating an example of the nano scale resonator of FIG. 2A including valleys.

Figure 1:
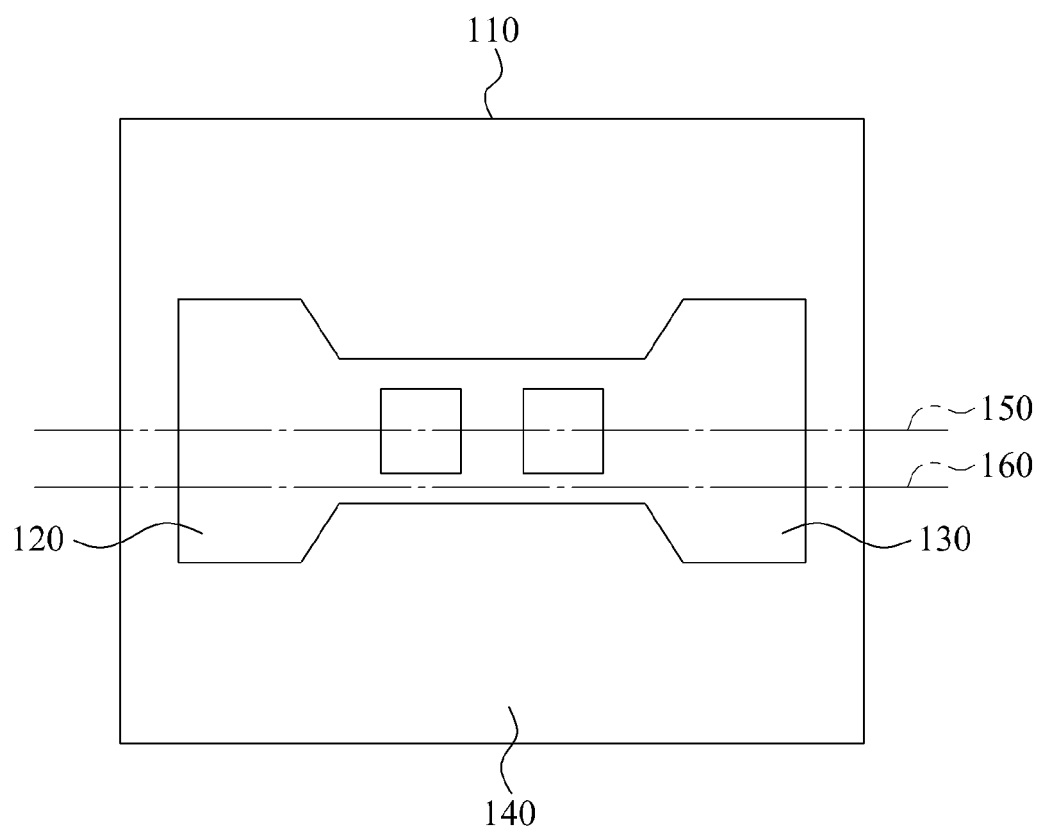
FIG. 1 is a top view illustrating an example of a nano scale resonator.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

A planar type resonator may be fabricated using a micro electro mechanical systems (MEMS) process, a clamped type resonator, a patterning scheme using a scanning probe microscope (SPM), a scheme of growing particles of nano scale, and any other fabrication scheme for a planar type resonator known to one of ordinary skill in the art.

A planar type resonator based on a MEMS process is configured on a thin membrane film. Therefore, when fabricating the planar type resonator based on the MEMS process, a thin film is likely to be destroyed due to stress and other forces known to one of ordinary skill in the art that are caused as a result of high temperature, high pressure, and other severe process conditions known to one of ordinary skill in the art. As such, the overall fabrication process may be difficult.

In the case of a clamped type resonator, a capacitor is present between a beam and a lower electrode. A beam is transformed based on a bias, a transformation of a capacitor occurring due to the transformation of beam, and a change in a resonant frequency.

In the case of a cantilever type resonator, the resonator is fabricated to be small in order to increase a quality factor (Q) value. As a result, an existing ultraviolet lithography process may have some constraints in fabrication.

A device fabricated using an SPM has a very minute structure. However, fabrication using an SPM is a relatively long process. As such, mass production of the resultant planar type resonators may be difficult.

In the case of a scheme of creating a suspended type structure by growing nano scale particles, a nano structure with a small line width may be fabricated. However, fabrication of a plurality of nano structures and subsequent arrangement of the fabricated plurality of nano structures during a growth process may be difficult. That is, it may be difficult to appropriately grow nano scale particles having a desired length and direction.

FIG. 1 is a top view illustrating an example of a nano scale resonator 110. Referring to the example illustrated in FIG. 1, the nano scale resonator 110 includes a first electrode 120, a second electrode 130, and a substrate 140. A structure of an anchor, an air gap, and a resonance unit that are disposed on the substrate 140 will be further described with reference to FIGS. 2A and 2B. Herein, the nano scale means the nanometer scale.

In an example, a signal is transferred to another electrode without being lost when a predetermined frequency signal is applied to the first electrode 120 or the second electrode 130. In an example, a radio frequency (RF) signal is applied to the first electrode 120 or the second electrode 130.

The nano scale resonator 110 is based on a resonance phenomenon. In an example, when physical periodicity of the nano scale resonator 110 matches periodicity of a signal applied to the nano scale resonator 110, the nano scale resonator 110 preserves or transfers energy of a frequency corresponding to a matching period without loss. In a further example, the nano scale resonator 110 selects and processes a predetermined frequency comment using a frequency selective characteristic.

In an example, the resonance phenomenon occurs when a signal is applied having an equal period to that of a natural frequency of the nano scale resonator 110. In a further example, the natural frequency is determined based on mass of the nano scale resonator 110, spring hardness, and a damping level. In yet another example, the natural frequency is determined through determination of a line width of the nano scale resonator 110.

A Q value should be considered when fabricating the nano scale resonator 110. In an example, when 3 dB to both sides based on a resonant frequency, or an interval between frequencies of a point at which energy is offset to be a half, is a 3 dB bandwidth, the Q value is obtained by dividing the resonant frequency by the 3 dB bandwidth. An increase in the Q value may sharpen a resonance characteristic and improve the selective characteristic quality.

In an example, in order to increase a Q value, a hardness of the nano scale resonator 110 is increased or a mass of the nano scale resonator 110 is decreased. In another example, the mass of the nano scale resonator 110 is decreased by fabricating the nano scale resonator 110 to have a minute line width. In yet another example, the nano scale resonator 110 having the minute line width is configured through a laser interference lithography (LIL) process.

The LIL process is able to form a nano structure using an interference phenomenon between laser beams. In an example, the LIL process is based on a characteristic in which a grid pattern of nano scale is formed due to interference between two laser beams during emission of the two laser beams on photoresist after application of the photoresist on a substrate, the photoresist being a photosensitive material.

The LIL process enables configuration of a device of a nano scale line width and fabrication of a device in a form of a three-dimensional (3D) bridge.

A nano scale device fabricated based on the LIL process may be applicable to a resonator, a biosensor, and other various fields known to one of ordinary skill in the art.

FIG. 2A is a cross-sectional view illustrating an example of a nano scale resonator. For example, FIG. 2A shows a cross-section 150 of the nano scale resonator 110 of FIG. 1. Referring to the example illustrated in FIG. 2A, the nano scale resonator includes a resonance unit 210, an air gap 220, and anchors 231 and 233.

In the example illustrated in FIG. 2A, the resonance unit 210 includes a first electrode 261, a second electrode 263, resonance layers 251 and 253, and a sub resonance unit 211. In an example, the first electrode 261 and the second electrode 263 are a single block together with the resonance unit 210 in a functional aspect. In another example, the first electrode 261 and the second electrode 263 are treated as separate constituent elements in a fabrication aspect. In yet another example, the resonance unit 210 is formed as nano scale based on an LIL process using an interference pattern of light.

In an example, the air gap 220 is adjacent to a substrate 240. Further, the anchors 231 and 233 are disposed on the substrate 240. In another example, to enhance a reflective characteristic of vertical waves occurring in the resonance layers 251 and 253 and the sub resonance unit 211 of nano scale, the resonance unit 210 is separated from the substrate 240 through the air gap 220. In yet another example, the sub resonance unit 211 of nano scale is formed through an LIL process.

In an example, to enhance a reflective characteristic or a transmission characteristic in a resonant frequency band, the resonance unit 210 includes a plurality of sub resonance units 211 that are arranged on a plane and connected to a common electrode.

In an example, the air gap 220 is formed by depositing a photoresist film on the substrate 240, etching the photoresist film through patterning to form a cavity, forming a sacrificial layer on the cavity, sequentially depositing a membrane layer, a resonance layer, and a conductive material on the sacrificial layer and the substrate 240, and etching the sacrificial layer.

In another example, the air gap 220 is formed by forming a sacrificial layer on the substrate 240, patterning the formed sacrificial layer, forming an insulating film on the patterned sacrificial layer and the substrate 240, sequentially depositing a resonance layer and a conductive material on the substrate 240, and removing the patterned sacrificial layer. In a furtherance of this example, the sacrificial layer is removed by injecting etchant through a via-hole that is connected from outside of a device to the sacrificial layer disposed within the device. In an additional furtherance of this example, the air gap 220 is formed in a position at which the sacrificial layer is removed.

The air gap 220 is empty and, thus, impedance is close to being infinite. Waves occurring in the resonance layers 251 and 253 and the sub resonance unit 211 may remain within the resonance layers 251 and 253 and the sub resonance unit 211 without being lost by the air gap 220.

In an example, the air gap 220 is formed on the substrate 240 using a sacrificial layer that is patterned to fit a shape of the air gap 220. Here, the anchors 231 and 233 are formed. In an example, the anchors 231 and 233 and the air gap 220 are formed using the sacrificial layer, which is common to the anchors 231 and 233 and the air gap 220. In another example, a portion of the sacrificial layer corresponding to the air gap 220 is removed from the sacrificial layer formed on the substrate 240 through patterning, and a remaining sacrificial layer is formed as the anchors 231 and 233.

In an example, the sacrificial layer is formed using a silicon oxide based material, a silicon nitride based material, and a metal based material. In another example, poly silicon (Si), which has a high resistivity characteristic of about tens of thousands kΩcm, is used for the sacrificial layer.

In an example, the first electrode 261 and the second electrode 263 are formed using gold, molybdenum, ruthenium, aluminum, platinum, titanium, tungsten, palladium, chrome, nickel, and other similar metals known to one of ordinary skill in the art.

In an example, the sub resonance unit 211 is formed in one of a linear shape, a circular shape, and a serpent shape, with the shape of the sub resonance unit 211 being determined based on an interference pattern of the LIL process.

In an example, the anchors 231 and 233 are formed of a material having resistivity greater than or equal to 10 kΩcm. When resistivity of the anchors 231 and 233 is greater than or equal to 10 kΩcm, waves occurring in the resonance layers 251 and 253 and the sub resonance unit 211 remain within the resonance layers 251 and 253 and the sub resonance unit 211 without being lost by the anchors 231, 233 and the air gap 220.

In an example, the air gap 220 is formed by removing the sacrificial layer through gas injected via a release hole (not shown). In this example, the injected gas is an etchant in a vapor state and is used to remove the sacrificial layer.

FIG. 2B is a cross-sectional view illustrating an example of the nano scale resonator of FIG. 2A including valleys 271 and 273. Referring to the example illustrated in FIG. 2B, the anchors 231 and 233 and the air gap 220 are formed by etching a sacrificial layer portion corresponding to the air gap 220 based on valleys 271 and 273 in the sacrificial layer formed on the substrate 240. In a further example, the sacrificial layer is patterned to fit a shape of the valleys 271 and 273 that is a boundary between the air gap 220 and the anchors 231 and 233. The valleys 271 and 273 are formed by forming the sacrificial layer, forming photoresist on the sacrificial layer using deposition, removing photoresist of a portion corresponding to the valleys 271 and 273, and etching the sacrificial layer to fit the shape of the valleys 271 and 273.

In an example, the valleys 271 and 273 prevent the injected gas from entering areas of the anchors 231 and 233. Accordingly, in an example, the air gap 220 is formed by removing a sacrificial layer portion corresponding to the air gap 220 through the injected gas. The air gap 220 and the anchors 231 and 233 are formed from a single sacrificial layer.

Figure 3:
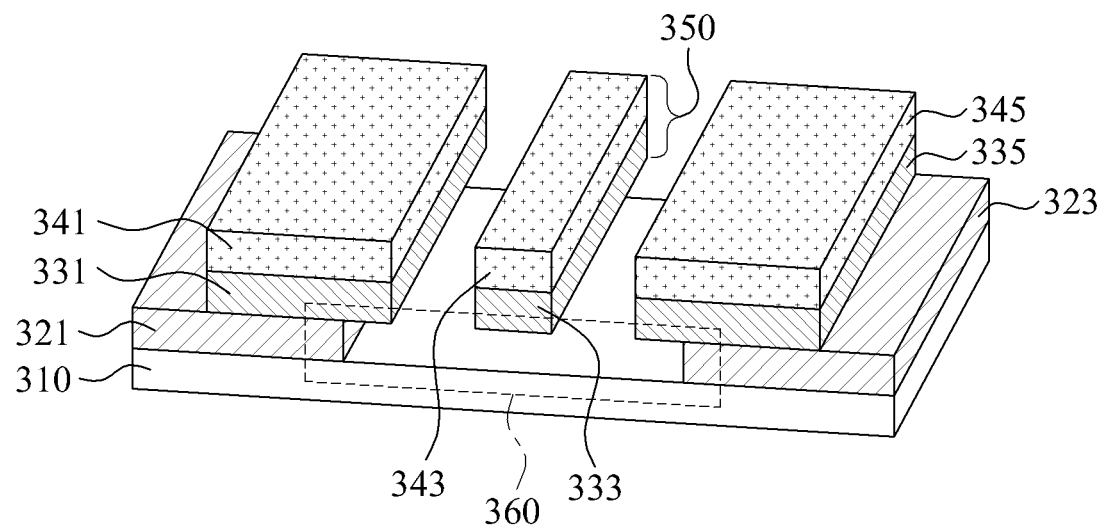
FIG. 3 is a perspective view illustrating another example of a nano scale resonator.

FIG. 3 is a perspective view illustrating another example of a nano scale resonator. For example, FIG. 3 illustrates a three-dimensional (3D) structure of the nano scale resonator of the example illustrated in FIG. 2A.

Referring to the example illustrated in FIG. 3, the nano scale resonator includes an air gap 360, anchors 321 and 323, and a sub resonance unit 350. The anchors 321 and 323 and the air gap 360 are disposed on a substrate 310. In an example, the air gap 360 and the anchors 321 and 323 are formed using the same sacrificial layer. A portion that is removed from the sacrificial layer formed on the substrate 310 through etching corresponds to the air gap 360. A remaining portion of the sacrificial layer that is not removed corresponds to the anchors 321 and 323.

In an example, a resonance layer 331 and a first electrode 341 are disposed on the anchor 321 and the air gap 360. In a further example, when a predetermined frequency signal is applied to the first electrode 341, a resonance phenomenon occurs in the resonance layer 331.

In yet another example, a resonance layer 335 and a second electrode 345 are disposed on the anchor 323 and the air gap 360. When a resonance phenomenon occurs in the resonance layer 331, a predetermined frequency wave is transferred to the resonance layer 335 and the predetermined frequency signal is output through the second electrode 345.

The sub resonance unit 350 is disposed on the air gap 360, and includes a resonance layer 333 and a conductive layer 343. In an example, the resonance layer 333 is formed between the resonance layers 331 and 335 through patterning by the LIL process. Even though not illustrated in FIG. 3, in another example, the resonance layers 331, 333, and 335 are connected to each other in a predetermined area. As a result, a wave occurring in the resonance layer 333 is transferred to the resonance layer 335.

In an example, a plurality of sub resonance units 350 is disposed on the air gap 360. When a width of the sub resonance unit 350 decreased and a number of sub resonance units 350 having the narrow width increases, a Q value of a nano scale resonator escalates.

Figure 4:
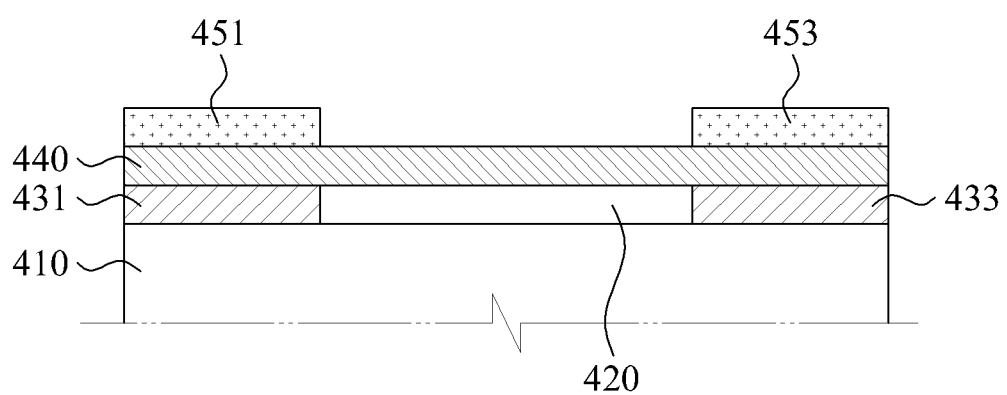
FIG. 4 is a cross-sectional view illustrating another example of a nano scale resonator.

FIG. 4 is a cross-sectional view illustrating another example of a nano scale resonator. For example, FIG. 4 illustrates a cross-section 160 of FIG. 1. Referring to the example illustrated in FIG. 4, the nano scale resonator includes an air gap 420, anchors 431 and 433, a resonance layer 440, a first electrode 451, and a second electrode 453. In this example, the air gap 420 and the anchors 431 and 433 are disposed on a substrate 410 and are formed using a sacrificial layer common to the air gap 420 and the anchors 431 and 433, thereby avoiding fabrication costs of using multiple sacrificial layers.

In an example, the resonance layer 440 resonates based on a frequency of a signal input to the first electrode 451. In this resonance, a predetermined frequency wave is transferred to the second electrode 453. In a further example, a partial area of the resonance layer 440 is patterned to nano scale through an LIL process and etched, thereby serving to form an empty space.

In an example, the air gap 420 may reflect a vertical wave occurring in the resonance layer 440. The anchors 431 and 433 support the resonance layer 440.

Figure 5:
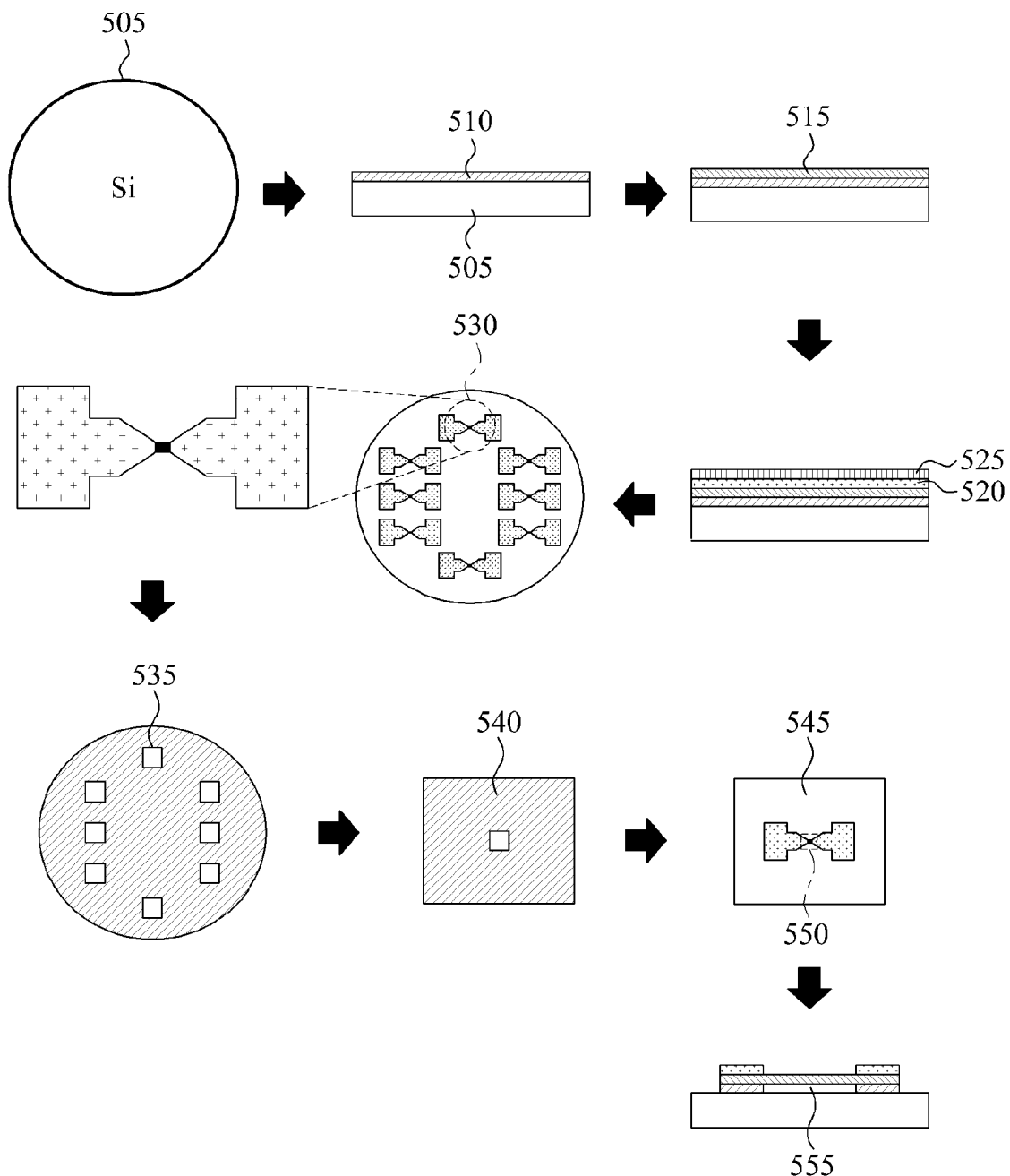
FIG. 5 is a diagram illustrating an example of a fabrication process of a nano scale resonator.

FIG. 5 is a diagram illustrating an example of a fabrication process of a nano scale resonator. Referring to the example illustrated in FIG. 5, the nano scale resonator is fabricated based on a silicon substrate 505 or a silicon on insulator (SOI) substrate.

A thin film 510 to be used as an insulating and sacrificial layer is deposited on the silicon substrate 505. In an example, the thin film 510 may include a silicon oxide based material or a silicon nitride based material. In another example, the silicon oxide based material is formed through a heat treatment and plasma enhanced chemical vapor deposition (PECVD) process, and the silicon oxide based material is formed through a PECVD and low pressure chemical vapor deposition (LPCVD) process. The thin film 510 has a thickness that is greater than or equal to about 1 μm.

A resonance layer 515 is deposited after deposition of the thin film 510. In an example, nano scale patterning is performed on the resonance layer 515. In another example, the resonance layer 515 includes poly silicon, silicon nitride, a metal based material, or other materials known to one of ordinary skill in the art, based on a use of a resonator and an available process. When the resonance layer 515 is formed on the sacrificial layer, the resonance layer 515 and the sacrificial layer are distinguishable from each other, thereby enabling deposition to be performed based on different materials.

A conductive layer 520 configured to measure a signal of a device is formed on the resonance layer 515. In this example, the conductive layer 520 is formed by employing, as a constituent material, Ti/Au, Cr/Au, and other appropriate conductive materials known to one of ordinary skill in the art.

A masking layer 525 is formed on the conductive layer 520 to prevent loss from occurring due to an etchant during a process. In general, various materials may be used for the masking layer 525. For example, chrome, silicon nitride, silicon oxide, and other masking materials known to one of ordinary skill in the art may be used.

In an example, a patterning process is applied to fabricate the nano scale resonator. In one example, a general ultraviolet (UV) lithography process is used to pattern the conductive layer 520.

An LIL process uses LIL dedicated resist. As a result, the LIL dedicated resist is deposited overall on a patterned conductive layer 530.

In the LIL process, a laser is emitted toward a portion where the nano scale resonator is configured, instead of toward the overall substrate 505. Accordingly, a portion 535 toward which a laser is emitted is opened. In an example, the portion 535 is opened using a separate mask and UV lithography.

FIG. 5 describes an example in which the LIL process loads a chip 540 having a maximum size of about 2 cm×2 cm. Therefore, in this example, the LIL process proceeds through dicing into a chip shape. However, in an example in which equipment loadable to the entire wafer is used, the LIL process is performed by loading the whole substrate without a separate dicing process.

After the LIL process, a linear shape 550 of nano scale is fabricated by developing LIL dedicated resist 545.

In an example, the sub resonance unit of nano scale is formed by etching the patterned conductive layer 530 and resonance layer 515 through a reactive ion etching (RIE) process. After the RIE process, an air gap 555 and anchors is formed by removing the sacrificial area. The resonance layer 515 disposed on the air gap 555 is patterned to be nano scale through the LIL process. When the sacrificial layer is removed using wet-typed etchant, the resonance layer 515 in a nano scale structure does not endure the flow of etchant and is destroyed.

Accordingly, a sacrificial layer removal process is performed in a state where the etchant is in a vapor state. In an example, when silicon oxide is used for the sacrificial layer, buffered oxide etchant (BOE) or potassium hydroxide (KOH) in a vapor state is used for etching. In another example, a predetermined thickness of the sacrificial layer is secured so that the vapor may be well smeared. In a further example, when the process proceeds with a circulation system so that the etchant may well flow in order to form the air gap 555, it is further effective in forming the air gap 555. In yet another example, by forming the air gap 555, the nano scale resonator is fabricated in a form of a suspended bridge.

In an example in which an SOI wafer is used for a substrate, a process of forming a sacrificial layer and a resonance layer is omitted and the following process is the same.

In an example, a patterning process is performed using deposition to form a separate conductive layer for signal processing and other purposes known to one of ordinary skill in the art. In another example, the patterning process of the separate conductive layer is not be used. In this case, deposition is performed to a resonance layer without forming a conductive layer. That is, without forming the conductive layer and performing the patterning process, the above process is performed alike.

When fabricating a device in a form of a suspended bridge, there is a need to appropriately adjust a thickness, a length, and a width of a resonance layer based on a use thereof.

Figure 6:
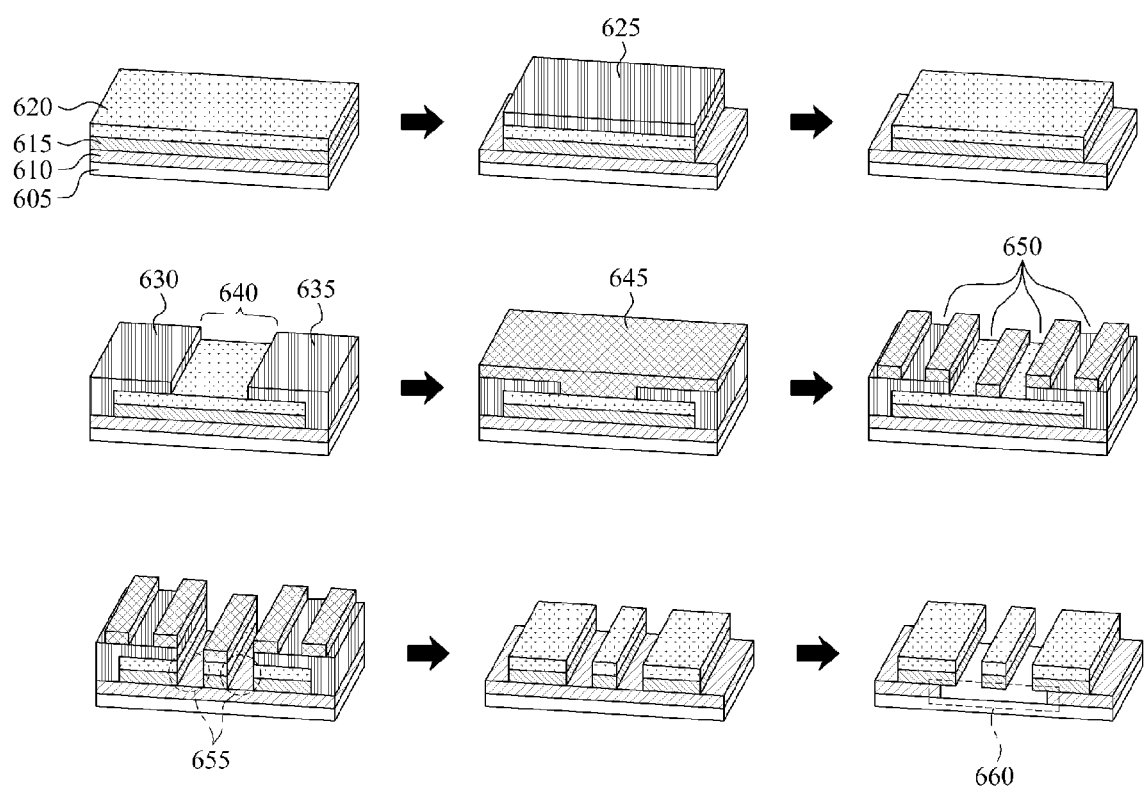
FIG. 6 is a diagram illustrating another example of a fabrication process of a nano scale resonator.

FIG. 6 is a diagram illustrating another example of a fabrication process of a nano scale resonator. Referring to the example illustrated in FIG. 6, the nano scale resonator is fabricated based on a silicon substrate 605. Silicon oxide is formed as a sacrificial layer 610 on the silicon substrate 605 using deposition. Poly silicon is formed as a resonance layer 615 on the sacrificial layer 610 using deposition. Chrome is formed as a conductive layer 620 on the resonance layer 615 using deposition.

When photoresist 625 is formed on the conductive layer 620 using deposition, a shape of the nano scale resonator is formed on the conductive layer 620 through patterning. When photoresist layers 630 and 635 are formed using deposition after removing the photoresist 625, a portion 640 at which an LIL process is to be performed is opened through a UV lithography process.

LIL dedicated resist 645 is deposited on the open area 640 and the photoresist 630 and 635. Portions 650 each having a nano scale width are formed on the LIL dedicated resist 645 through LIL patterning.

A sub resonance unit is disposed between areas 655 by etching a portion unprotected with the photoresist 630 and 635 among the portions 650 each having the nano scale width through RIE.

When the LIL dedicated resist 645 and the photoresist 630 and 635 are removed, an air gap 660 is formed by removing the sacrificial layer 610 using etchant in a vapor state. The nano scale resonator is fabricated in a form that the sub resonant unit is separated from the substrate 610 through the air gap 660.

Figure 7:
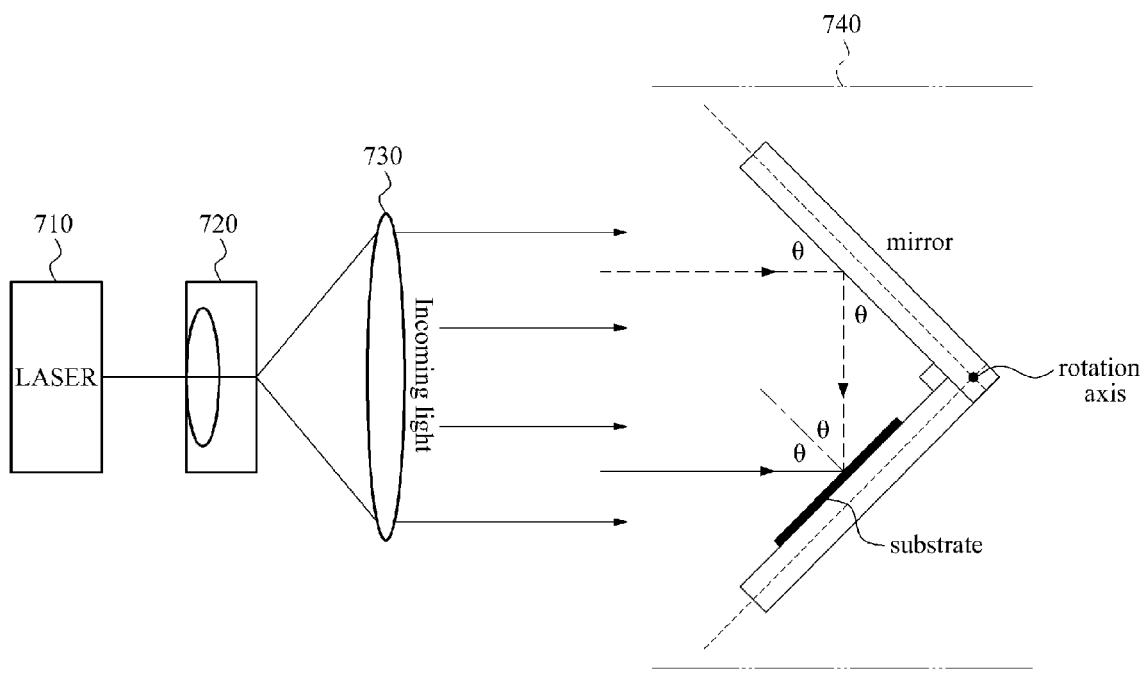
FIG. 7 is a diagram illustrating an example of a fabrication of a nano scale resonator based on a laser interference lithography process.

FIG. 7 is a diagram illustrating an example of a fabrication of a nano scale resonator based on a laser interference lithography process. In the example illustrated in FIG. 7, a device of nano scale is fabricated by generating an interference phenomenon between an incident wave and a reflected wave on the surface of a substrate using a single layer beam during the LIL process.

A first example method of forming an interference field to apply the interference phenomenon of a laser beam to lithography generates interference by splitting a laser beam into two directions. In an example, each of the split beams, which are split into two directions through a beam splitter, passes a spatial filter. While passing the spatial filter, diameters of the beams are expanded. The expanded beams generate interference on the substrate and thereby form an interference pattern on a photoresist that is applied on the substrate. Adjustment of an incident angle of each beam with respect to the substrate serves to adjust a period of the interference pattern.

A second example method of forming an interference field to apply the interference phenomenon of a laser beam to lithography uses Lloyd's mirror interferometer 740. In an example, an interference pattern is formed by fixing a full reflection mirror and a supporter to which a substrate is mountable to have a vertical angle between the full reflection mirror and the supporter, and emitting a laser beam towards the substrate. In another example, an angle of beam directly incident to the substrate and an angle of beam reflected from the mirror and then incident to the substrate are identical to each other. In yet another example, even though an angle of a beam that is directly incident to the substrate varies, an incident angle of a beam reflected from the mirror is the same as the angle of a beam incident to the substrate at all times.

An angle of beam incident to the substrate is adjusted by rotating the mirror interferometer 740 along a rotation axis. As the angle of beam is adjusted, a period of the interference pattern formed on the substrate varies.

Referring to the example illustrated in FIG. 7, a diameter of a laser beam output from a laser generation apparatus 710 is expanded while passing a spatial filter 720. The expanded laser beam passes through a lens 730 to be incident to a mirror interferometer 740.

Figure 8:
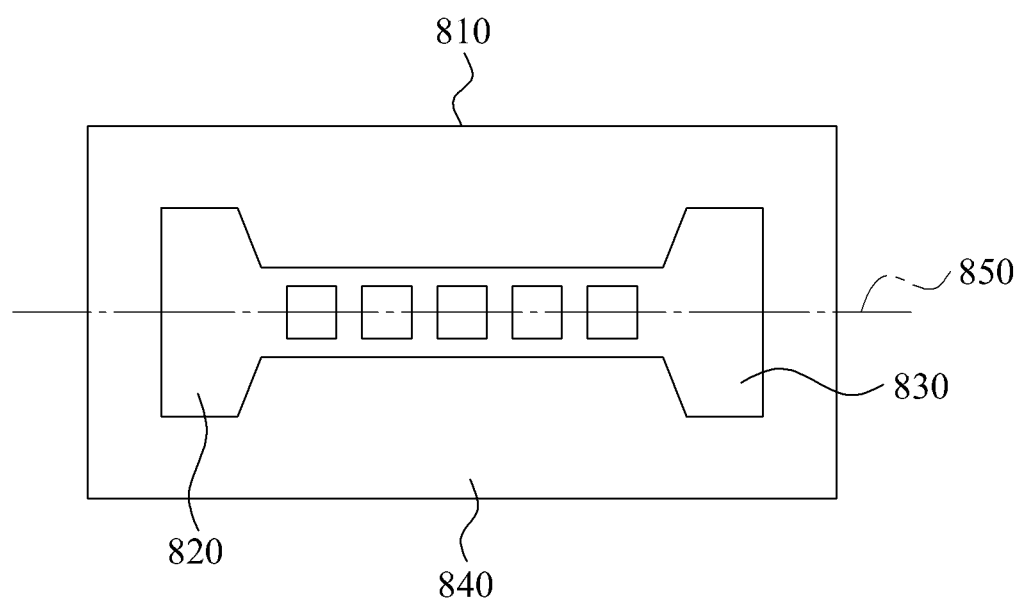
FIG. 8 is a top view illustrating an example of a nano scale sensor.

FIG. 8 is a top view illustrating an example of a nano scale sensor. Referring to the example illustrated in FIG. 8, the nano scale sensor 810 includes a first electrode 820, a second electrode 830, and an anchor, an air gap, and a sensing unit that are disposed on a substrate 840. A structure of the anchor, the air gap, and the sensing unit will be further described with reference to FIG. 9.

In an example, when a predetermined frequency signal is applied to the first electrode 820 or the second electrode 830, the signal is transferred without loss to another electrode. In another example, the signal to be applied is based on an RF signal.

A resonance layer is disposed below the first electrode 820 and the second electrode 830. In an example, the resonance layer resonates when a predetermined frequency signal is applied to the first electrode 820 or the second electrode 830.

In an example, a resonant frequency varies, or electric current flowing in the first electrode 820 or the second electrode 830 varies based on a bonding material to be combined with a surface processed material of the sensing unit. In another example, resistance of the sensing unit varies based on the bonding material, whereby, in yet another example, an amount of current flowing from the first electrode 820 to the second electrode 830 varies. In still another example, mass of the sensing unit varies based on the bonding material, whereby, in another further example, the resonant frequency that resonates in the resonance layer varies.

In an example, the sensing unit senses the bonding material based on a change amount of current or a change amount of resonant frequency. Sensing accuracy is enhanced when a Q value increases.

In an example, a method of increasing hardness of the nano scale sensor 810 or decreasing mass of the nano scale sensor 810 is employed to increase a Q value. In a further example, the mass is decreased by fabricating the nano scale sensor 810 to have a minute line width. In yet another example, the nano scale sensor 810 having the minute line width is configured through an LIL process.

An LIL process is a technology of forming a nano structure using an interference phenomenon between laser beams. In an example, the LIL is based on a characteristic in which a grid pattern of nano scale is formed due to interference between two laser beams when emitting the two laser beams on photoresist after applying the photoresist, where the photoresist is a photosensitive material on a substrate.

Figure 9:
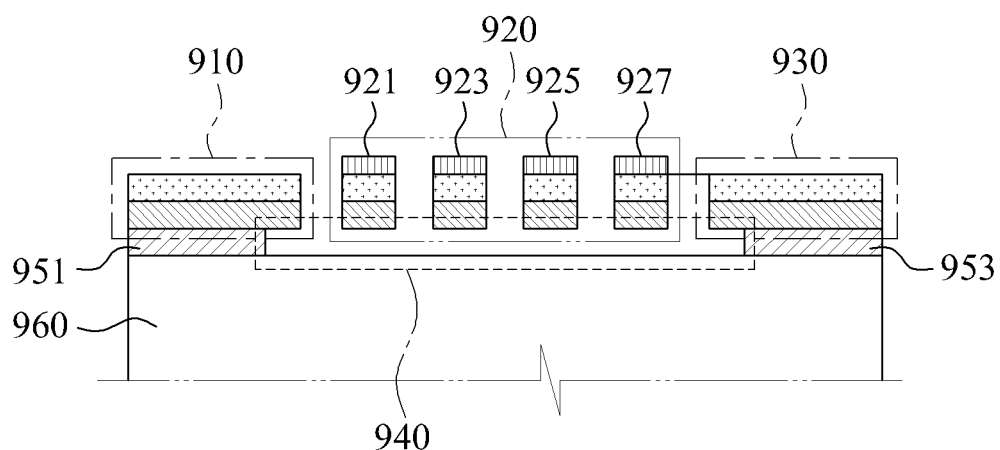
FIG. 9 is a cross-sectional view illustrating an example of a nano scale sensor.

FIG. 9 is a cross-sectional view illustrating an example of a nano scale sensor. FIG. 9 shows a cross-section 850 of FIG. 8. Referring to the example illustrated in FIG. 9, the nano scale sensor includes a first electrode 910, a sensing unit 920, a second electrode 930, an air gap 940, and anchors 951 and 953. The sensing unit 920 additionally includes a plurality of sub sensing units 921, 923, 925, and 927. In an example, the sensing unit 920 may be formed as nano scale based on an LIL process using an interference pattern of light.

In an example, a biomaterial is processed on the plurality of sub sensing units 921, 923, 925, and 927. In a further example, the biomaterial is combined with a predetermined material.

In an example, when different materials are processed on the respective sub sensing units 921, 923, 925, and 927, the sensing unit 920 senses the different materials. In another example, when a single material is processed on each of the plurality of sub sensing units 921, 923, 925, and 927, the sensing unit 920 senses the single material.

In an example, the sensing unit 920 senses a predetermined material based on a scheme of sensing a change in current and a scheme of measuring a shifted level of resonant frequency. In another example, the sensing unit 920 senses a change in current by sensing a change in resistance that, in yet another example, occurs due to combination of the predetermined material and the biomaterial processed on the plurality of sub sensing units 921, 923, 925, and 927.

In an example, when the biomaterial and the predetermined material are combined with each other, mass of the plurality of sub sensing units 921, 923, 925, and 927 varies. Due to the change in mass, in another example, a change occurs in resonant frequencies generated by the plurality of sub sensing units 921, 923, 925, and 927. Accordingly, in yet another example, the sensing unit 920 senses the predetermined material based on a change amount of resonant frequency.

The air gap 940 and the anchors 951 and 953 are disposed on a substrate 960. In an example, the air gap 940 and the anchors 951 and 953 is formed using a sacrificial layer common to the air gap 940 and the anchors 951 and 953. In another example, the air gap 940 prevents external loss of waves by reflecting a vertical component among waves of resonant frequencies generated by the plurality of sub sensing units 921, 923, 925, and 927.

In an example, when a biomaterial is processed on the first electrode 910 and the second electrode 930, the first electrode 910 and the second electrode 930 functions as the sensing unit 920. In another example, the anchors 951 and 953 support the first electrode 910, the second electrode 930, and the sensing unit 920. Even though not illustrated in FIG. 9, in yet another example, the plurality of sub sensing units 921, 923, 925, and 927 is connected using a resonant material or a conductive material.

Figure 10:
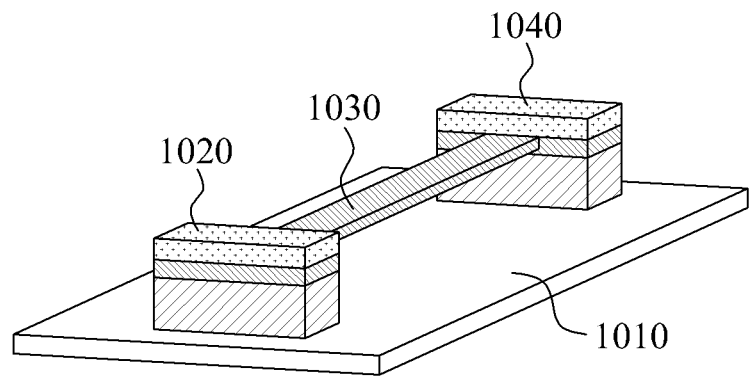
FIGS. 10, 11, and 12 are perspective views illustrating yet another example of a nano scale resonator.
Figure 11:
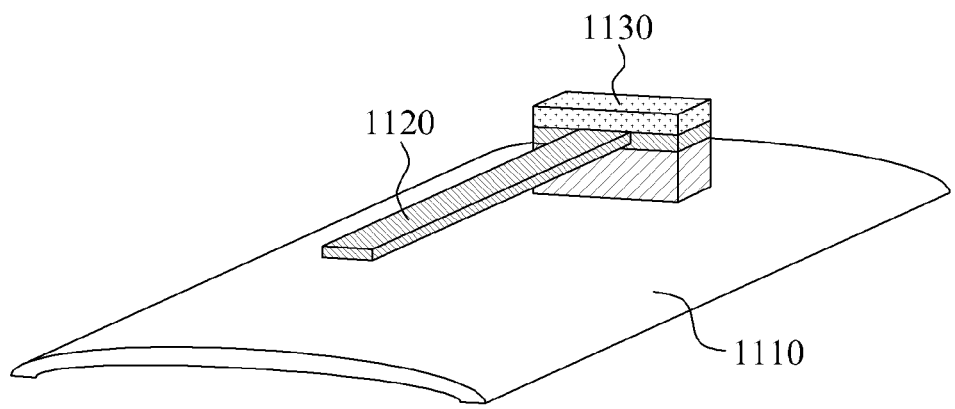
Figure 12:
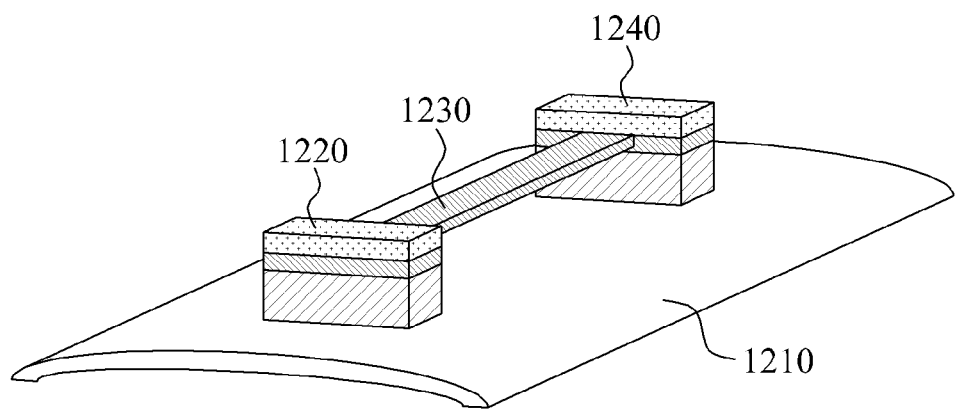

FIGS. 10 through 12 are perspective views illustrating yet another example of a nano scale resonator.

FIG. 10 is a diagram illustrating an example of a nano scale resonator in a bridge form that is formed on a fixed substrate 1010. An input end 1020 and an output end 1040 are disposed on the fixed substrate 1010, and a resonance layer 1030 is disposed between the input end 1020 and the output end 1040. In an example, an RF signal is applied to the input end 1020. In an example, when a signal matching a resonant frequency of the resonance layer 1030 is input, a resonance phenomenon occurs and an RF signal is output through the output end 1040. Here, in another example, patterning is performed on the resonance layer 1030 through an LIL process. In yet another example, sub resonance units formed as nano scale are disposed on the resonance layer 1030.

FIG. 11 is a diagram illustrating an example of a nano scale resonator in a cantilever form that is formed on a flexible substrate 1110. A measurement end 1130 capable of applying an RF signal and measuring a response of the applied RF signal is disposed on the flexible substrate 1110. One end of the resonance layer 1120 is connected to the measurement end 1130. In an example, a length of the resonance layer 1120 is determined based on a width of the resonance layer 1120.

FIG. 12 is a diagram illustrating an example of a nano scale resonator in a bridge form that is formed on a flexible substrate 1210. An input end 1220 and an output end 1240 are disposed on the flexible substrate 1210, and a resonance layer 1230 is disposed between the input end 1220 and the output end 1240. Here, in an example, nano scale patterning is performed on the resonance layer 1230 through an LIL process. In another example, sub resonance units formed as nano scale are disposed on the resonance layer 1230.

According to the teachings above, there is provided a nano scale resonator that, in using an air gap and an anchor that have the same height, may enhance degradation in a determination characteristic of a resonance layer occurring due to a gradient structure.

In addition, according to the teachings above, there is provided a nano scale resonator that may be employed as an information communication device and a sensor used to detect a predetermined characteristic in a bio field.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A nano scale resonator, comprising:
   a nano scale resonance unit, configured to resonate based on an applied signal, and comprising
   one or more nano scale sub resonance units having a surface processed material, wherein the surface processed material is configured to sense a bonding material, based on a change in resistance in the surface processed material caused by the bonding material; and
   an anchor disposed on a substrate and under the nano scale resonance unit, the anchor configured to support the nano scale resonance unit, and the anchor having an air gap disposed within boundaries of the anchor, the nano scale resonance unit, and the substrate,
   wherein the air gap is configured to reflect a vertical wave occurring in the nano scale resonance unit.

2. The nano scale resonator of claim 1, wherein the resonance unit further comprises:
   a resonance layer;
   a first electrode disposed on the resonance layer; and
   a second electrode disposed on the resonance layer,
   wherein the first electrode is configured to receive the applied signal, the resonance layer is configured to resonate a signal based on the received signal, and the second electrode is configured to output the resonated signal.

3. The nano scale resonator of claim 2, wherein the resonance layer comprises poly silicon, silicon nitride, or a metal based material.

4. The nano scale resonator of claim 1, wherein the anchor comprises a material having a resistivity that is greater than or equal to 10 kΩcm.

5. The nano scale resonator of claim 1, wherein the one or more nano scale sub resonance units comprise a linear shape, a circular shape, or a serpent shape.

6. A nano scale sensor, comprising:
   a nano scale sensing unit having a surface processed material, wherein the surface processed material is configured to sense a bonding material, based on a change in resistance in the surface processed material caused by the bonding material; and
   an anchor disposed on a substrate, the anchor configured to support the sensing unit, the anchor having an air gap disposed within boundaries of the anchor, the sensing unit, and the substrate, and the air gap configured to reflect a vertical wave occurring in the sensing unit.

7. The nano scale sensor of claim 6, wherein the sensing unit comprises one or more nano scale sub sensing units.

* * * * *